United States Patent [19]

Schembri

[11] Patent Number: 5,173,193

[45] Date of Patent: Dec. 22, 1992

[54] CENTRIFUGAL ROTOR HAVING FLOW PARTITION

[76] Inventor: Carol T. Schembri, 3912 Marshall Ave., San Mateo, Calif. 94403

[21] Appl. No.: 678,823

[22] Filed: Apr. 1, 1991

[51] Int. Cl.$^5$ .............................. G01N 1/28; B04B 5/12; B01D 21/26

[52] U.S. Cl. .................................. 210/782; 210/745; 210/95; 210/198.1; 210/380.1; 210/513; 422/64; 422/72; 422/101; 422/102; 436/45; 436/63; 436/177; 436/180

[58] Field of Search ............ 210/94, 95, 198.1, 380.1, 210/514, 515, 745, 782, 787, 789; 422/64, 72, 101, 102; 436/45, 63, 177, 180; 494/16, 27, 29, 37, 43; 356/246, 426

[56] References Cited

U.S. PATENT DOCUMENTS

| | | | |
|---|---|---|---|
| 3,795,451 | 3/1974 | Mailen | 356/246 |
| 3,864,089 | 2/1975 | Tiffany et al. | 23/258.5 |
| 3,899,296 | 8/1975 | Mailen et al. | 494/10 |
| 3,901,658 | 8/1975 | Burtis et al. | 494/16 |
| 4,279,862 | 7/1981 | Bretaudiere et al. | 422/72 |
| 4,284,602 | 8/1981 | Kelton et al. | 494/10 |
| 4,469,793 | 9/1984 | Guigan | 436/45 |
| 4,509,856 | 4/1985 | Lee | 356/246 |
| 4,515,889 | 5/1985 | Klose et al. | 435/4 |
| 4,689,203 | 8/1987 | Kaartinen et al. | 422/72 |
| 4,847,205 | 7/1989 | Burtis et al. | 422/72 |
| 4,894,204 | 1/1990 | Cornut | 422/72 |

Primary Examiner—W. Gary Jones

[57] ABSTRACT

The present invention provides a centrifugal rotor which measures and delivers a predetermined volume of fluid to a receiving chamber in the rotor. The rotor comprises a bulk fluid chamber containing a bulk amount of fluid and a metering chamber which has a predetermined volume. The bulk fluid flowing into the metering chamber fills the chamber and excess fluid flows out into an overflow chamber. Thus, a predetermined volume is obtained. This volume is delivered to the receiving chamber through an exit duct which prevents flow at the rotational speed required to fill the metering chamber but allows flow at a second, higher rotational speed. The exit duct is typically a capillary in which capillary forces prevent flow until the rotational speed is increased.

21 Claims, 3 Drawing Sheets

CENTRIFUGAL ROTOR HAVING FLOW PARTITION

The present invention is related to the inventions disclosed in the following copending applications: Ser. No. 07/532,524, Ser. No. 07/678,824 and Ser. No. 07/678,762, the disclosures of which are incorporated herein by reference.

BACKGROUND OF THE INVENTION

1. Field of the Invention

The present invention relates generally to devices and methods for optically analyzing biological fluids. In particular, it relates to the design and use of centrifugal rotors which allow precise measurement and delivery of a predetermined volume of a fluid to a chamber in the rotor.

Blood plasma and other biological tests frequently require that liquids be quickly divided into predetermined volumes for analysis in a variety of optical tests or assays. It is also frequently desirable to separate potentially-interfering cellular components of the material from the biological fluid prior to testing. Such measurement and separation steps have heretofore been typically performed by centrifugation to separate, for instance, blood plasma from the cellular components, followed by manual or automated pipetting of predetermined volumes of the blood plasma into separate test wells. Such procedures are labor intensive and time-consuming, and various automated systems and methods have been proposed for providing multiple aliquots of plasma suitable for testing in a more efficient manner.

Of particular interest to the present invention are centrifugal rotors which have been modified both to measure volumes of fluid, such as blood, followed by mixture of the fluid with an appropriate diluent and/or separation of fluid from cellular components. Such rotors can additionally provide a plurality of discrete volumes in separate test wells which may be optically tested or evaluated.

Prior art rotors have frequently utilized complex designs which are difficult and costly to manufacture. Often, the rotors require various separable parts or components which are brought together or separated at different points in the centrifugation procedure. Previous centrifugal rotors have often been limited in the number of discrete samples and test wells which they can provide, and in some cases require the use of a separate displacement fluid to effect flow of blood and plasma through the system.

For these reasons, it would be desirable to provide improved centrifugal rotors and methods suitable for quickly and easily measuring a predetermined volume of fluid, delivering the predetermined volume of fluid into, for example, chambers suitable for separation of cellular components and ultimately distributing the fluid into test wells within the rotors for analysis. Additionally, the rotors should be capable of measuring and distributing relatively small volumes of fluid.

The rotors should be able to accommodate relatively large numbers of test wells or cuvettes, and the rotor design should be simple and amenable to low-cost manufacturing procedures. In particular, it would be desirable if the rotors were of unitary construction with no separable or movable parts. Liquid measurement separation methods should be simple and be capable of being performed in relatively short times. In particular, the methods should require relatively few steps and should be capable of being performed with little or no intervention or manipulations by the operator. It would be particularly desirable if the methods required only rotation of the rotor in order to effect measurement and delivery of the fluid.

2. Description of the Background Art

U.S. Pat. No. 4,894,204 discloses a centrifugal rotor having a calibration vessel connected to an overflow vessel. The calibration vessel has a feed orifice through which it communicates with a central receptacle and an exit orifice located in the wall opposite the feed orifice. The exit orifice is designed such that liquid begins to escape from the calibration vessel from the start of its being filled. U.S. Pat. No. 4,284,602 describes a centrifugal rotor in which measuring chambers are positioned between an inlet and the reaction chamber. An overflow chamber is provided to receive excess fluid. Flow from the measuring chamber, however, is effected by use of a heavier displacement fluid, rather than by an increased rotational speed. U.S. Pat. No. 3,899,296 describes a rotor for performing photometric analyses of whole blood samples in which the cellular component is separated from the plasma and measured subvolumes of the plasma are distributed to sample analysis cuvettes. Delivery of the measured volumes is obtained by applying a slight positive air pressure to the passageways containing the plasma. U.S. Pat. No. 4,469,793 relates to centrifugal rotor having a measurement chamber having inlet and outlet orifices. The outlet orifice leads to passages which carry liquid to an overflow chamber when the rotor is rotating in a first direction and to a receptor cell when the rotor is rotating in a second, opposite direction.

The following patents do not provide for measurement of a predetermined volume of fluid as the rotor spins. U.S. Pat. No. 3,864,089 describes a rotor for blood fractionation. U.S. Pat. No. 4,279,862 is directed to a rotor which has means for creating a pressure differential and/or turbulence to produce a homogeneous mixture of reagent and sample. U.S. Pat. No. 4,509,856 is directed to a rotor useful for photometric analysis of a sample. U.S. Pat. No. 4,515,889 relates to the rotor having a plurality of interconnected small hollow spaces adapted for mixing reaction components. U.S. Pat. No. 4,689,203 relates to a centrifugal rotor designed for separating blood plasma from red and white blood cells.

SUMMARY OF THE INVENTION

In accordance with the present invention, a centrifugal rotor is provided which is adapted for measurement and delivery of a predetermined volume of fluid. The rotor comprises a bulk fluid chamber containing a bulk amount of fluid to be partitioned and a metering chamber connected to the bulk fluid chamber positioned radially outward from the bulk fluid chamber such that fluid enters the metering chamber as the rotor is spun. An overflow chamber is connected to the metering chamber for receiving excess fluid after the metering chamber is filled. The volume of the fluid remaining in the metering chamber corresponds to the predetermined volume. Either a biological fluid, such as whole blood, or a reagent, such as a diluent, may be placed in the bulk fluid chamber.

A receiving chamber is positioned radially outward from the metering chamber and is connected to the metering chamber through a connecting means which prevents flow of fluid into the receiving chamber until the metering chamber contains the predetermined volume. The fluid can be held in the metering chamber for as long as desired before delivery to the receiving chamber. Typically, the connecting means is a capillary exit duct in which capillary forces prevent flow at a first rotational speed. At a second, higher rotational speed, centrifugal force exceeds the capillary force and the metering chamber is emptied. The connecting means can also be a siphon having an elbow that is substantially the same distance from the center of the rotor as the radially most inward point of the metering chamber. As the rotor is spinning the fluid does not flow past the elbow. After the rotor stops, capillary forces "prime" the siphon by pulling fluid just around the elbow. When the rotor is restarted, the combination of centrifugal and capillary forces draw the remaining fluid out of the metering chamber into the receiving chamber.

The receiving chamber is typically a separation chamber having a cell trap for separating cellular material from blood plasma. The separated plasma typically is distributed to a collection chamber which is connected to a plurality of cuvettes in which the biological fluid is analyzed.

The rotor of the present invention is preferably made of clear plastic, more preferably acrylic. Each cuvette typically contains reagents necessary for a biochemical analysis of the fluid in the cuvette. The biochemical analysis preferably produces an optical effect when exposed to a light beam which is then detected and analyzed.

Other advantages of the subject invention will be apparent to those skilled in the art from consideration of the detailed description of the preferred embodiments of the subject invention set forth below and of the attached drawings.

DESCRIPTION OF THE SPECIFIC EMBODIMENTS

Figure 1:
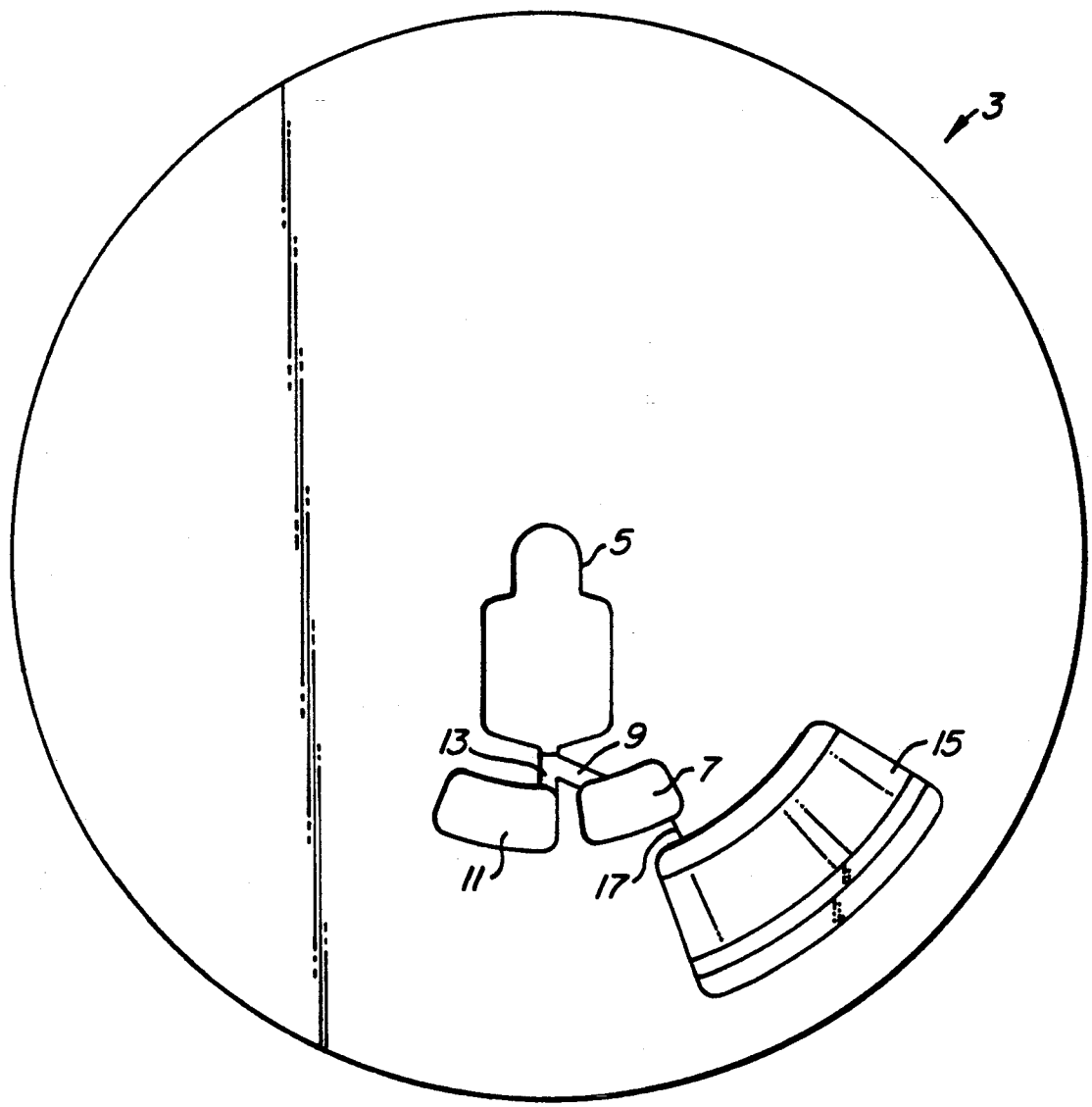
FIG. 1 is a plan view of a rotor designed in accordance with one embodiment of the present invention in which the metering chamber is used to measure a precise volume of blood.

The present invention provides devices and methods for measuring and delivering predetermined volumes of fluid, such as a diluent or a biological fluid, to a receiving chamber in a centrifugal rotor. The measurement of the fluid is provided by a metering chamber of predetermined volume which is connected to a bulk fluid chamber. The bulk fluid chamber may contain a diluent, or other reagent, which is preloaded in the rotor for storage until the rotor is used. Alternatively, the bulk fluid chamber may be a capillary chamber which receives a biological fluid to be tested, for example blood. The fluid flowing into the metering chamber from the bulk fluid chamber fills the metering chamber, while excess fluid flows out of the metering chamber into an overflow chamber.

The predetermined volume in the metering chamber is delivered to the receiving chamber through at least one connecting means which controls flow out of the metering chamber so that fluid is delivered to the receiving chamber only after some predetermined time. Typically, delivery is delayed until after the metering chamber is filled and it contains the predetermined volume of fluid. The connecting means is designed such that essentially no detectable fluid escapes from the metering chamber until it is emptied. No detectable fluid is considered to have escaped from the metering chamber if the total volume of fluid ultimately delivered to the receiving chamber is sufficiently accurate such that subsequent analyses are not adversely affected.

The prevention of flow between the metering chamber and the receiving chamber can be accomplished in a number of ways. For instance, a capillary exit duct in which capillary forces prevent flow at a first rotational speed can be used. When the speed is increased to a second, higher rotational speed, centrifugal force exceeds the capillary force and the metering chamber is emptied. Other means can also be used to block flow at the first speed, for example, a membrane which ruptures only at the higher rotational speed can be inserted in the duct.

Other embodiments utilize a siphon having an elbow which is at substantially the same distance from the center of the rotor as the minimum radial point (i.e., the radially most inward point) of the metering chamber. After the metering chamber is filled and the rotor is stopped, capillary action pulls the fluid just beyond the elbow. A siphon in which the fluid has moved to this point as a result of capillary action is considered to be "primed". The rotor is restarted and the combination of centrifugal and capillary forces pulls the fluid out of the metering chamber and into the receiving chamber.

It is also possible to serialize several metering chambers in a single rotor. Fluid overflowing from a first metering chamber enters a second metering chamber of a precise, predetermined size. The excess from the second metering chamber then overflows into a third metering chamber, etc. Each metering chamber in the rotor typically feeds a separate receiving chamber.

If the fluid is one which contains cellular material, such as whole blood, the receiving chamber is usually a separation chamber designed to separate fluid (e.g., plasma) from cellular material. The separation chamber is typically also connected to a diluent metering chamber which delivers a predetermined volume of diluent to be mixed with the plasma. Various diluents known to those skilled in the art are suitable for use in the present invention. For instance, standard diluents such as normal saline solution (0.5% NaCl in water), phosphate buffered solution, and Ringer's lactate solution and the like may be used. The rotor also provides for distribution of the diluted plasma into a plurality of test wells or cuvettes so that different optical analytic procedures may be performed without having to transfer aliquots of the plasma from the apparatus. All of the above steps preferably occur as a result of centrifugal force generated by the spinning rotor.

The apparatus is very easy to manufacture and can be produced at a very low cost, making the apparatus suitable for use as a disposable in testing whole-blood samples. The apparatus can provide for automatic combination of the separated plasma with a predetermined volume of reagent or diluent and can apportion substantially equal volumes of plasma among the plurality of cuvettes. More importantly, the apparatus is suitable for use with a variety of conventional analytic measurement devices, such as spectrophotometers and fluorometers, which allow the plasma in the cuvettes to be individually examined without the need to remove the plasma.

Although the present invention is particularly suitable for analyzing diluted or undiluted blood plasma, it will be useful with a wide variety of other biological fluids, such as urine, sputum, semen, saliva, ocular lens fluid, cerebral fluid, spinal fluid, amniotic fluid, and tissue culture media, as well as food and industrial chemicals, and the like. Where it may be desirable to separate cells and other interfering substances prior to analysis or assay, the devices and methods described in copending application, U.S. Ser. No. 532,524 (which is incorporated herein by reference) are preferably used. That application discloses a centrifugal rotor for separating plasma from whole blood which includes a plurality of internal chambers and passages for combining the plasma with one or more reagents and distributing the plasma to a plurality of individual test wells. The chambers and passages necessary for separating the whole blood into plasma are located radially outward from the metering chamber. The separation chamber includes a radially-outward cell trap and a radially-inward drainage port so that spinning of the rotor causes the cellular components of the whole blood to enter the cell trap, while cessation of spinning allows the separated plasma to flow downward through the drainage port. A collection chamber is formed at a lower level than the rotor to receive the plasma through the drainage port. In the present invention, the collection chamber can also be located on the same level as the separation chamber an d separated plasma can flow to the collection chamber by means of centrifugal, rather than gravitational, force.

The distribution of fluid to cuvettes or test wells is preferably accomplished using the methods and devices disclosed in copending application U.S. Ser. No. 07/678,824, which is incorporated herein by reference. In that application, a centrifugal rotor comprising a plurality of peripheral cuvettes spaced radially outward from the collection chamber is disclosed. A plurality of generally radial inlet channels connects each cuvette to the chamber. Each inlet channel has a discrete flow path for fluid to enter the cuvette and another discrete flow path for gas to exit the cuvette as the cuvette is filled. As the rotor is spun, fluid enters the cuvettes from the collection chamber through the inlet channels, which also allow gas in the cuvettes to escape, thus avoiding the creation of bubbles in the cuvette as the cuvettes are filled. Positioned radially inward from each cuvette is a reflective surface capable of deflecting a light beam between a generally vertical direction and a generally horizontal (typically radial) direction. The contents of each cuvette are typically optically analyzed by passing a light beam vertically through the rotor and deflecting the beam in a radial direction to pass through the cuvette.

The apparatus of the present invention includes a centrifugal rotor which is capable of being mounted on a conventional laboratory centrifuge of the type which is commercially available from suppliers, such as Beckman Instruments, Inc., Spinco Division, Fullerton, California; Fisher Scientific, Pittsburgh, Pennsylvania; VWR Scientific, San Francisco, California, and the like. Generally, the centrifugal rotors will include a receptacle or other coupling device suitable for mounting on a vertical drive shaft within the centrifuge. The particular design of the receptacle or coupling device will depend on the nature of the centrifuge, and it will be appreciated that the centrifugal rotor of the present invention may be adapted to be used with most types of centrifuges which are now available or which may become available in the future so long as the velocity profile can be programmed.

The centrifugal rotor comprises a body structure which maintains a desired geometric pattern or relationship between a plurality of chambers and interconnecting inlet channels, as described in more detail hereinbelow. Usually, the body will be a substantially solid plate with the chambers and passages formed as spaces or voids in an otherwise solid matrix. Conveniently, such solid plate structures may be formed by laminating a plurality of separately formed layers together into a composite structure where the chambers and passages are generally formed between adjacent layers. The individual layers may be formed by injection molding, machining, and combinations thereof, and will usually be joined together, typically using a suitable adhesive or by ultrasonic welding. The final enclosed volumes are formed when the layers are brought together. Of course, the centrifugal rotor could also be formed as a plurality of discrete components, such as tubes, vessels, chambers, etc., arranged in a suitable structural framework. Such assemblies, however, are generally more difficult to manufacture and are therefore less desirable than those formed in a substantially solid plate.

The centrifugal rotor may be formed from a wide variety of materials and may optionally include two or more materials. Usually, the materials will be transparent, for example clear plastic, so that the presence and distribution of blood, plasma, and other reagents, may be observed within the various internal chambers and passages. Also, it is generally required that the test wells formed within the rotor have suitable optical paths formed therethrough so that the contents of the test well may be observed spectrophotometrically, fluorometrically, or by other visual assessment instruments. In the exemplary embodiment described below, the rotor is formed from acrylic resins having the required optical properties, at least in those areas which define the optical paths.

The apparatus and method of the present invention are suitable for performing a wide variety of analytic procedures which are beneficially or necessarily performed on blood plasma. The analytic procedures will generally require that the blood plasma be combined with one or more reagents so that some optically detectable change occurs in the plasma which may be related to measurement of a particular component or characteristic of the plasma. Preferably, the plasma will undergo a reaction or other change which results in a change in color, fluorescence, luminescence, or the like, which may be measured by conventional spectrophotometers, fluorometers, light detectors, etc. In some cases, immunoassays and other specific binding assays may be performed in the test wells. Generally, however, such assay procedures must be homogeneous and not require a separation step. In other cases, it will be possible to accommodate heterogeneous assay systems by providing a means to separate blood plasma from the test wells after an immunological reaction step has occurred.

Conventional blood assays which may be performed include glucose, lactate dehydrogenase, serum glutamic-oxaloacetic transaminase (SGOT), serum glutamic-pyruvic transaminase (SGPT), blood urea (nitrogen) (BUN), total protein, alkalinity, phosphatase, bilirubin, calcium, chloride, sodium, potassium, magnesium, and the like. This list is not exhaustive and is intended merely as being exemplary of the assays which may be performed using the apparatus and method of the present invention. Usually, these tests will require that the blood plasma be combined with one or more reagents which result in an optionally detectable, usually photometrically detectable, change in the plasma. The reagents which are required are well known and amply described in the patent and scientific literature.

Figure 2:
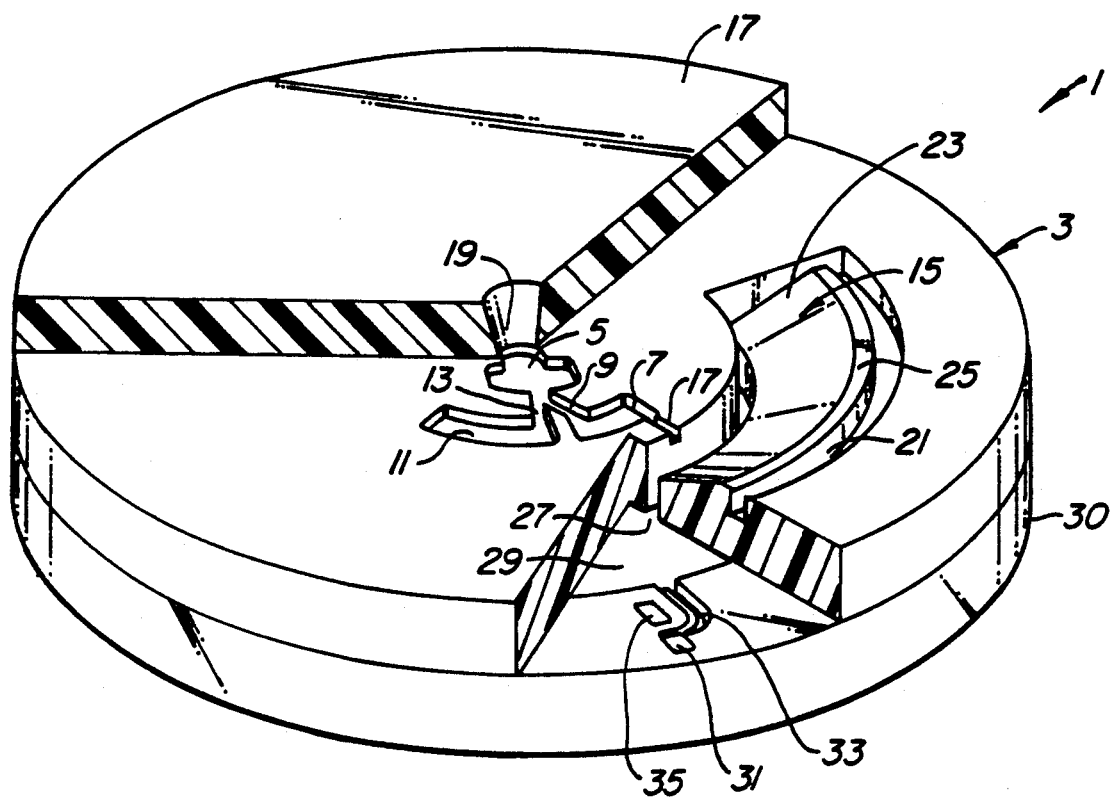
FIG. 2 is a perspective view, vertically sectioned, showing the three layers of a rotor of FIG. 1.

Referring now to FIGS. 1 and 2, a cylindrical rotor 1 constructed in accordance with the principles of the present invention is shown in detail. The rotor 1 is in the form of a substantially solid disk, the middle layer 3 of which is shown in FIG. 1. The middle layer 3 comprises a blood capillary 5 and a metering chamber 7 connected to the blood capillary 5 by a connecting channel 9. An overflow chamber 11 is connected to the metering chamber 7 through the overflow channel 13. The blood capillary 5, the metering chamber 7 and overflow chamber 11 preferably have capillary dimensions. An initial volume of fluid, such as whole blood, is introduced into the blood capillary 5 through blood application port 19 (shown in FIG. 2). As the rotor spins the initial volume partitions between the metering chamber 7 and the overflow chamber 11. The metering chamber 7 is sized to accept the predetermined amount of fluid desired to be split from the blood capillary 5. The first fluid entering the metering chamber 7 will fill the chamber, while excess fluid will overflow the metering chamber 7 and flow through connecting channel 9 and overflow channel 13 into overflow chamber 11. The overflow feature causes the original bulk amount of fluid to be split into two amounts, the first precisely measured amount and the excess fluid.

The fluid entering the metering chamber 7 is delivered to a separation chamber 15 through an exit duct 17. The exit duct is typically of capillary dimensions which prevent flow of fluid at rotational speeds which cause filling of the metering chamber 7. For whole blood or diluent, the diameter of the capillary exit duct 17 is typically between about 0.05 mm and about 0.25 mm, preferably between about 0.075 mm and about 0.125 mm. The rotational speeds to fill the metering chamber typically generate a centrifugal force of about $5 \times g$ to about $42 \times g$, preferably about $20 \times g$ to about $27 \times g$. To deliver fluid to the separation chamber 15 after the metering chamber is filled, the rotor's speed is increased sufficiently to cause the centrifugal force to exceed the capillary force and thus drain the metering chamber 7 into the separation chamber 15. The higher rotational speeds are typically generate a centrifugal force exceeding about $45 \times g$.

The top layer 17 and bottom layer, 30 of the rotor are also shown in FIG. 2. The top layer includes a blood application port 19 which penetrates the entire thickness of the top layer 17 and is aligned with the blood capillary 5. The blood application port 19 may conveniently be formed in the top layer 17 by machining, e.g., drilling.

The components of the separation chamber 15 are also shown to include a cell trap 21 formed at its radially-outward periphery and a receptacle region 23 formed along its radially-inward perimeter. A capillary region 25 is formed between the receptacle region 23 and the cell trap 21 in order to inhibit the backflow of cells after they have entered the cell trap 21 as a result of centrifugal separation. The receptacle region 23 provides a volume which is capable of receiving whole blood or other biological fluid (typically combined with a diluent or reagent) and which retains the blood plasma or other separated fluid after centrifugation has been completed. An axial port 27 is conveniently formed as an annular passage which penetrates the entire thickness of middle layer 3 so that separated plasma may flow downward from receptacle region 23 of separation chamber 15 into the collection chamber 29 formed in bottom layer 30. As discussed above, the collection chamber need not be positioned below the separation chamber. It can, for example, be positioned radially outward of the separation chamber.

The collection chamber 29 is spaced radially inward from a plurality of peripheral cuvettes 31 (only one of which is shown in FIG. 2). Each cuvette 31 is connected to the collection chamber 29 by an inlet channel 33. Each inlet channel 33 comprises two discrete flow paths which allow gas to escape easily from the cuvette 31 a it is filled and thus prevent the formation of bubbles in the cuvette 31, which can deleteriously affect the results of optical analyses.

Optical analysis of the cuvette contents is facilitated by reflective surfaces 35 positioned radially inward from each cuvette 31 and are capable of deflecting a light beam between a generally horizontal and a generally vertical direction.

Figure 3:
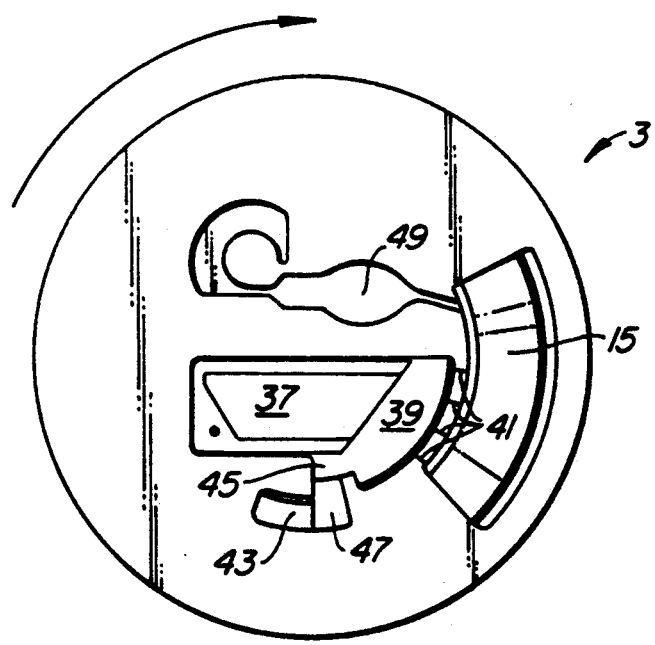
FIG. 3 is a plan view of a rotor in which the metering chamber is used for diluent.

FIG. 3 shows another embodiment of the middle layer 3 the present invention in which a diluent chamber 37 containing a bulk amount of diluent is connected to a diluent metering chamber 39, which is connected by a plurality of exit ducts 41 to the separation chamber 15. Typically, the diluent is preloaded in the rotor and stored in the rotor until use. A biological fluid, such as blood, is also delivered to the separation chamber 15 through a blood metering chamber 49. The blood metering chamber 49 functions in the same way as that described in copending application Ser. No. 07/678,762, supra.

The diluent metering chamber operates on the same principles as the metering chamber described in FIG. 1. As the rotor spins the initial bulk volume of diluent partitions between the diluent metering chamber 39 and the overflow chamber 43. The diluent metering chamber 39 is sized to accept the predetermined amount of fluid desired to be split from the diluent chamber 37. The diluent entering the diluent metering chamber 39 will fill the chamber, while excess diluent will overflow the diluent metering chamber 39 and flow through connecting channel 45 and overflow channel 47 into overflow chamber 45. The overflow feature causes the original bulk diluent to be split into two amounts, the precisely measured amount and the excess fluid.

To deliver the diluent to the separation chamber 15 after the diluent metering chamber 39 is filled, the rotor's speed is increased sufficiently to cause the centrifugal force to exceed the capillary force and thus drain the diluent metering chamber 39 into the separation chamber 15. The rotational speeds to fill and empty the diluent metering chamber 39 are preferably the same as those to fill and empty the metering chamber 7 and to measure the blood.

Figure 4:
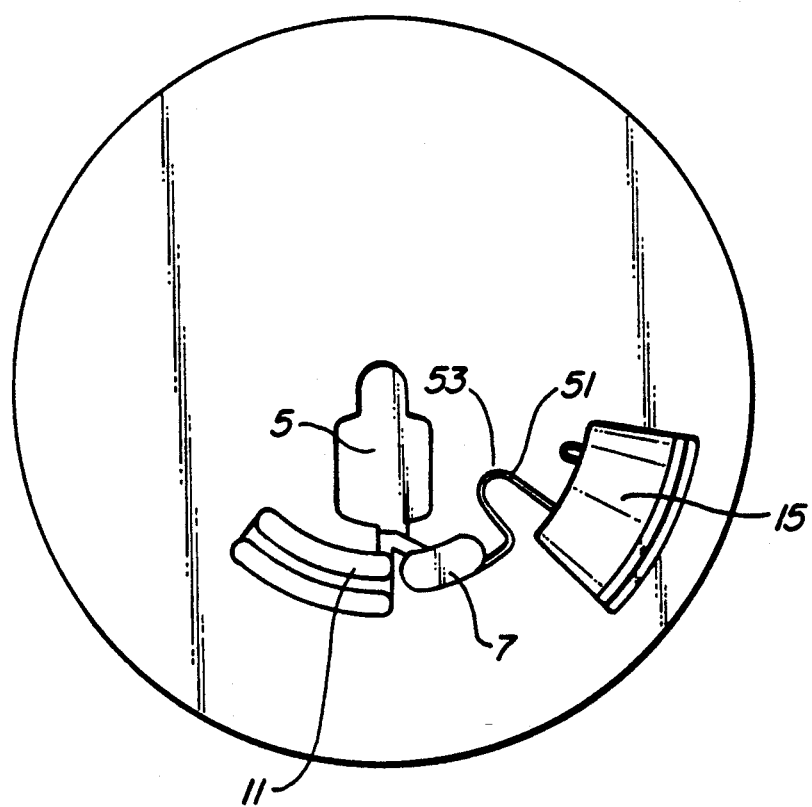
FIG. 4 is a plan view of a rotor in which a siphon is used to control flow between the metering chamber and the separation chamber.

Turning now to FIG. 4, a rotor using a siphon 51 as the connecting means to control flow between the metering chamber 7 and separation chamber 15 is shown.

The elbow 53 of the siphon 51 is positioned so that it is substantially the same distance from the center of the rotor 1 as the radially most inward point of the metering chamber 7.

As the rotor spins and the metering chamber 7 is filled, fluid in the siphon 51 does not move past the elbow 53. The rotor is then stopped and capillary action pulls fluid just beyond the elbow and the siphon is "primed." When the rotor is spun again, centrifugal and capillary forces pull the fluid out of the metering diameter 7 into the separation chamber 15.

The above description of the embodiments of the invention and the attached drawings are provided by way of illustration only, numerous other embodiments will be apparent to one of skill in the art. Thus, limitations on the scope of the subject invention are to be found only in the claims set forth below.

What is claimed is:

1. A centrifugal rotor comprising:
   a bulk fluid chamber adapted to receive a fluid;
   a metering chamber connected to the bulk fluid chamber, the metering chamber being positioned radially outward from the bulk fluid chamber such that fluid in the bulk fluid chamber enters the metering chamber at a first rotational speed;
   an overflow chamber connected to the metering chamber;
   a receiving chamber positioned radially outward from the metering chamber; and
   a capillary means for delivering the fluid from the metering chamber to the receiving chamber, the capillary means having a cross sectional area such that flow of fluid from the metering chamber to the receiving chamber is prevented at a first rotational speed and allowed at a second higher rotational speed.

2. A rotor of claim 1 wherein the fluid is a diluent.

3. A rotor of claim 2 wherein the bulk fluid chamber is a diluent chamber having a preloaded bulk amount of diluent.

4. A rotor of claim 1 wherein the fluid is a biological fluid.

5. A rotor of claim 4 wherein the biological fluid is whole blood.

6. A rotor of claim 5 wherein the bulk fluid chamber is a blood capillary having a means for introducing blood therein.

7. A rotor of claim 1 wherein the receiving chamber is a separation chamber having a cell trap.

8. A rotor of claim 7 further comprising a collection chamber connected to the separation chamber and a plurality of cuvettes disposed radially outward from the collection chamber.

9. A rotor of claim 8 wherein each cuvette contains reagents necessary for analysis of the fluid.

10. A rotor of claim 1 which is made from clear plastic.

11. A rotor of claim 1 which is injection molded.

12. A rotor of claim 1 which is machined.

13. A method for delivering a predetermined volume of fluid to a receiving chamber in a centrifugal rotor, the method comprising the steps of:
   introducing a volume of fluid greater than the predetermined volume into a bulk fluid chamber;
   spinning the rotor at a first rotational speed to effect the radially outward flow of the fluid from the bulk fluid chamber into a metering chamber such that excess fluid flows out of the metering chamber into an overflow chamber, and a predetermined volume of fluid remains in the metering chamber, and
   spinning the rotor at a second, higher rotational speed to effect the flow of the predetermined volume of fluid from the metering chamber into the receiving chamber, through a capillary means having a cross sectional area such that flow of fluid from metering chamber to the receiving chamber is prevented at the first rotational speed and allowed at the second rotational speed.

14. A method of claim 13 wherein the receiving chamber is a separation chamber having a cell trap.

15. A method of step 13 wherein the bulk fluid chamber is a diluent chamber and the step of introducing the fluid is carried out by preloading a diluent in the diluent chamber.

16. A method of claim 13 wherein the bulk fluid container is a blood capillary and the step of introducing the fluid is carried out by placing whole blood in the blood capillary.

17. A centrifugal rotor comprising
   a bulk fluid chamber adapted to receive a fluid;
   a metering chamber connected to the bulk fluid chamber, the metering chamber being positioned radially outward from the bulk fluid chamber such that fluid in the bulk fluid chamber enters the metering chamber as the rotor is spun;
   an overflow chamber connected to the metering chamber for receiving excess fluid from the metering chamber;
   a separation chamber, having a cell trap, positioned radially outward from the metering chamber; and
   a siphon through which the metering chamber communicates with the separation chamber, the siphon being capable of preventing flow of fluid out of the metering chamber until after the metering chamber is full.

18. A rotor of claim 17 further comprising a collection chamber connected to the separation chamber and a plurality of cuvettes connected to the collection chamber and being positioned radially outward from the collection chamber.

19. A method of analyzing whole blood in a centrifugal rotor, the method comprising:
   placing a bulk volume of whole blood in the rotor;
   spinning the rotor to effect the radial outward flow of the bulk volume into a metering chamber such that excess blood flows into an overflow chamber and a predetermined volume of blood remains in the metering chamber;
   delivering the predetermined volume of blood to a separation chamber having a cell trap for separating blood plasma from cellular components;
   delivering the blood plasma to a plurality of cuvettes;
   optically analyzing the blood plasma in the cuvettes.

20. A method of claim 19 wherein the step of delivering the predetermined volume of blood is carried out by the step of increasing the rotational speed of the rotor, thereby effecting the flow of blood from the metering chamber into the receiving chamber through a capillary exit duct connecting the metering chamber to the separation chamber.

21. A method of claim 19 wherein the step of delivering the predetermined volume of blood is carried out by the step of stopping the rotation of the rotor, thereby priming a siphon connecting the metering chamber to the separation chamber, followed by the step of spinning the rotor, thereby initiating the operation of the siphon and emptying the metering chamber.

* * * * *

UNITED STATES PATENT AND TRADEMARK OFFICE
CERTIFICATE OF CORRECTION

PATENT NO. : 5,173,193
DATED : Dec. 22, 1992
INVENTOR(S) : Schembri

It is certified that error appears in the above-identified patent and that said Letters Patent is hereby corrected as shown below:

On the title page, insert:

item [73] Assignee: Abaxis, Inc.,
Mountain View, CA--;

On the title page, in item [56] after "Primary Examiner--W. Gary Jones" insert:
--Attorney, Agent, or Firm—TOWNSEND and TOWNSEND--;

In column 5, line 35, delete "an d" and substitute therefor --and--;
In column 7, line 10, delete "optionally detectable" and substitute therefor --optically detectable--;
In column 8, line 32, delete "3 the present" and substitute therefor --3 of the present--;
In column 8, line 54, delete "chamber 45" and substitute therefor --chamber 43--; and
In column 10, claim 15, line 1, delete "step 13" and substitute therefor --claim 13--.

Signed and Sealed this

Ninth Day of November, 1993

Attest:

Attesting Officer

BRUCE LEHMAN

Commissioner of Patents and Trademarks